United States Patent
Kallio et al.

(10) Patent No.: US 11,797,248 B2
(45) Date of Patent: Oct. 24, 2023

(54) PROVISION OF CONTENT AND/OR FUNCTIONAL FEATURES TO WEARABLE DEVICES

(71) Applicant: Amer Sports Digital Services Oy, Vantaa (FI)

(72) Inventors: Janne Kallio, Vantaa (FI); Tuomas Hapola, Vantaa (FI); Erik Lindman, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

(21) Appl. No.: 17/670,548

(22) Filed: Feb. 14, 2022

(65) Prior Publication Data
US 2022/0276818 A1 Sep. 1, 2022

(30) Foreign Application Priority Data
Feb. 26, 2021 (FI) .................................... 20215211

(51) Int. Cl.
*G06F 3/14* (2006.01)
*G16H 40/67* (2018.01)
(Continued)

(52) U.S. Cl.
CPC .......... *G06F 3/14* (2013.01); *A63B 24/0062* (2013.01); *A63B 71/0622* (2013.01);
(Continued)

(58) Field of Classification Search
CPC .......... G06F 3/14; G06F 3/0482; G06F 3/011; G06F 1/163; G06F 3/014; A63B 24/0062; A63B 71/0622; G16H 40/67
See application file for complete search history.

(56) References Cited

U.S. PATENT DOCUMENTS

| 11,317,833 B2 * | 5/2022 | Williams | G06F 3/04847 |
| 2013/0106684 A1 * | 5/2013 | Weast | A63B 24/0059 345/156 |

(Continued)

FOREIGN PATENT DOCUMENTS

| WO | WO2016102416 A1 | 6/2016 |
| WO | WO2016142338 A1 | 9/2016 |

OTHER PUBLICATIONS

DC Rainmaker: TrainingPeaks new structured workout integration with garmin wearables—DC Rainmaker. 2017, pp. 1-11.

*Primary Examiner* — Cao H Nguyen
(74) *Attorney, Agent, or Firm* — Laine IP Oy

(57) ABSTRACT

There is provided a wearable device, comprising: at least one processing core; at least one memory including computer program code; the at least one memory and the computer program code configured to, with the at least one processing core, cause the wearable device to: receive one or more recipes being indicative of input elements for the computer program code, the input elements comprising at least one or more triggering events; one or more display templates; one or more content elements; receive user input for selection of a recipe of the one or more recipes; detect a triggering event corresponding to the one or more triggering events; in response to detecting the triggering event, provide the one or more content elements corresponding to the triggering event for display on a display of the wearable device according to a display template corresponding to the triggering event.

21 Claims, 9 Drawing Sheets

(51) Int. Cl.
  *A63B 24/00*    (2006.01)
  *A63B 71/06*    (2006.01)
  *G06F 3/0482*   (2013.01)
  *G06F 3/01*     (2006.01)

(52) U.S. Cl.
  CPC ........... G06F 3/0482 (2013.01); G16H 40/67 (2018.01); *G06F 3/011* (2013.01)

(56) References Cited

U.S. PATENT DOCUMENTS

| | | | |
|---|---|---|---|
| 2013/0110264 A1* | 5/2013 | Weast | A61B 5/681 |
| | | | 700/91 |
| 2015/0067811 A1* | 3/2015 | Agnew | H04L 63/0281 |
| | | | 726/9 |
| 2015/0120320 A1 | 4/2015 | Fateh | |
| 2015/0334772 A1 | 11/2015 | Wong et al. | |
| 2016/0063825 A1 | 3/2016 | Moussette et al. | |
| 2017/0093593 A1 | 3/2017 | Yang et al. | |
| 2017/0225034 A1 | 8/2017 | Kass et al. | |
| 2017/0365135 A1 | 12/2017 | Gupta et al. | |
| 2018/0000414 A1 | 1/2018 | Lowet et al. | |
| 2018/0140900 A1 | 5/2018 | Kim et al. | |
| 2018/0160925 A1 | 6/2018 | Kim et al. | |
| 2022/0157184 A1* | 5/2022 | Wilson | G06F 3/04883 |

* cited by examiner

400

"Strava segments" 460

| Triggering events | Display template | Headline | Parameter(s) shown | Actions |
|---|---|---|---|---|
| Location: no location | 3 field | "Strava segments" | Speed; Distance; Duration | - |
| Location: section start (lat&long) | Text field | "Start – Alpe d'Huez" | Headline | Alarm; Lap |
| Location: section between start and end | 3 field | "Alpe d'Huez" | Personal record – lap duration; Speed; Segment lenght – lap distance | - |
| Location: section end (lat&long) | 3 field | "End – Alpe d'Huez" | Personal record – previous lap duration; Previous lap speed; Previous lap average HR | Alarm; Lap |

410 — Triggering events
420 — Display template
430 — Headline
440 — Parameter(s) shown
450 — Actions

Fig. 4

PROVISION OF CONTENT AND/OR FUNCTIONAL FEATURES TO WEARABLE DEVICES

FIELD

Various example embodiments relate to wearable devices.

BACKGROUND

Various features in wearable devices may be implemented as embedded software, for example. The software is usually created in a plurality of versions which may be distributed with new devices and/or offered as updates to the wearable devices. In addition to embedded software, application software may be available for the wearable device. Developer of the software ensures that the features work with the device, for example via testing and removing possible bugs.

SUMMARY

According to some aspects, there is provided the subject-matter of the independent claims. Some example embodiments are defined in the dependent claims. The scope of protection sought for various example embodiments is set out by the independent claims. The example embodiments and features, if any, described in this specification that do not fall under the scope of the independent claims are to be interpreted as examples useful for understanding various example embodiments.

According to a first aspect, there is provided a wearable device, comprising: at least one processing core; at least one memory including computer program code; the at least one memory and the computer program code configured to, with the at least one processing core, cause the wearable device to: receive one or more recipes being indicative of input elements for the computer program code, the input elements comprising at least one or more triggering events; one or more display templates; and one or more content elements; receive user input for selection of a recipe of the one or more recipes; detect a triggering event corresponding to the one or more triggering events; and in response to detecting the triggering event, provide the one or more content elements corresponding to the triggering event for display on a display of the wearable device according to a display template corresponding to the triggering event.

According to a second aspect, there is provided a method comprising receiving, by a wearable device, one or more recipes being indicative of input elements for a computer program code stored in at least one memory of the wearable device, the input elements comprising at least one or more triggering events; one or more display templates; and one or more content elements; receiving user input for selection of a recipe of the one or more recipes; detecting a triggering event corresponding to the one or more triggering events; and in response to detecting the triggering event, providing the one or more content elements corresponding to the triggering event for display on a display of the wearable device according to a display template corresponding to the triggering event.

According to a third aspect, there is provided a non-transitory computer readable medium comprising program instructions that, when executed by at least one processor, cause a wearable device to perform at least the method of the second aspect.

According to a further aspect, there is provided a computer program configured to cause at least the method of the second aspect to be performed.

BRIEF DESCRIPTION OF THE DRAWINGS

FIG. 4 shows, by way of example, a recipe;

DETAILED DESCRIPTION

A system as disclosed herein is beneficial for third party services to have their features available in wearable devices in real time and without application development or software development by the third party services themselves. The system is based on logic where third party services may provide content and/or functionality to be used in wearable devices via a cloud application programming interface. Third party service may provide content and functionality in a recipe format specified beforehand, and the resulting recipe may be synched to the wearable device from the cloud application programming interface. The recipe defines, for example, triggering events on when to show content, display template defining how the content is shown, and content to be shown.

Figure 1:
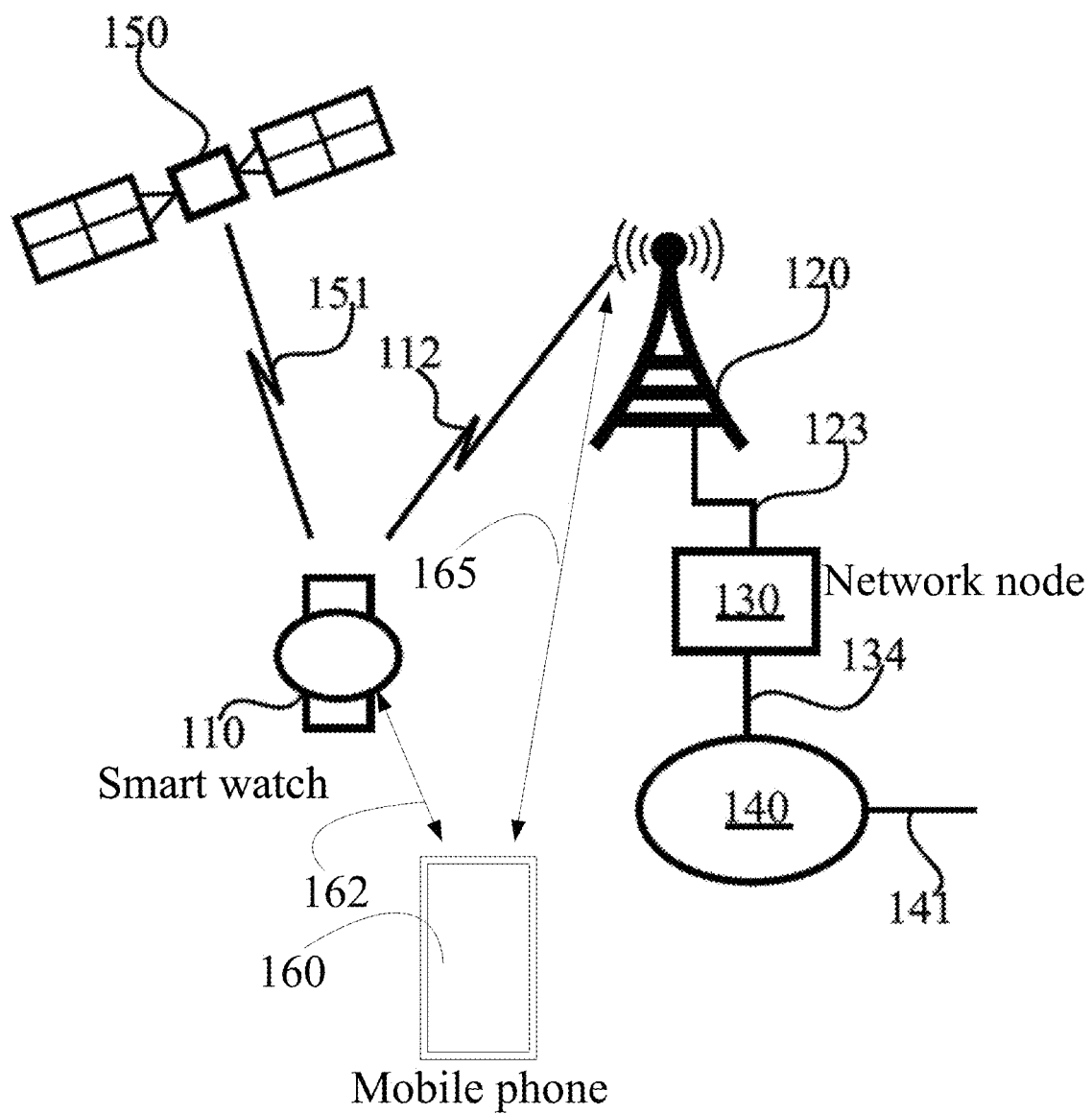
FIG. 1 shows, by way of example, a system.

FIG. 1 shows, by way of example, a system 100. The system comprises device 110, which may comprise, for example, a wearable device such as a smart watch, digital watch, or an activity bracelet. Device 110 may comprise a display, which may comprise a touchscreen display, for example. Device 110 may be powered, for example, by a rechargeable battery.

Device 110 may be communicatively coupled with a communications network. For example, in FIG. 1 device 110 is coupled, via wireless link 112, with base station 120. Base station 120 may comprise a cellular or non-cellular base station, wherein a non-cellular base station may be referred to as an access point. Examples of cellular technologies include wideband code division multiple access, WCDMA, and long term evolution, LTE, while examples of non-cellular technologies include wireless local area network, WLAN, and worldwide interoperability for microwave access, WiMAX. Base station 120 may be coupled with network node 130 via connection 123. Connection 123 may be a wire-line connection, for example. Network node 130 may comprise, for example, a controller or gateway device. Network node 130 may interface, via connection 134, with network 140, which may comprise, for example, the Internet or a corporate network. Network 140 may be coupled with further networks via connection 141. In some embodiments, device 110 is not configured to couple with base station 120. Network 140 may comprise, or be communicatively coupled, with a back-end server, for example.

Communication between the device 110 and the communication network may be realized via another user device, e.g. a mobile phone 160 or a personal computer such as a laptop. The device 110 may communicate with a user device via a wireless or wired connection. For example, the device 110 may communicate with the mobile phone 160 using a wireless connection 162 such as Bluetooth. The mobile phone 160 may have an application installed which may be configured to establish a communication connection 165 with the network such that the device 110 may, for example, receive data from the network and transmit data to the network via the mobile phone 160. As an example of a wired connection, the device 110 may be connected via a data cable, e.g. universal serial bus (USB) cable, to a laptop. The laptop may have a program installed which may be used to sync data between the device 110 and a web service in the network, for example.

Device 110 may be configured to receive, from satellite constellation 150, satellite positioning information via satellite link 151. The satellite constellation may comprise, for example the global positioning system, GPS, or the Galileo constellation. Satellite constellation 150 may comprise more than one satellite, although only one satellite is illustrated in FIG. 1 for the sake of clarity. Likewise, receiving the positioning information over satellite link 151 may comprise receiving data from more than one satellite.

Alternatively or additionally to receiving data from a satellite constellation, device 110 may obtain positioning information by interacting with a network in which base station 120 is comprised. For example, cellular networks may employ various ways to position a device, such as trilateration, multilateration or positioning based on an identity of a base station with which attachment is possible or ongoing. Likewise a non-cellular base station, or access point, may know its own location and provide it to device 110, enabling device 110 to position itself within communication range of this access point. The device 110 may be part of an indoor positioning system employing wireless technologies such as Bluetooth or Wi-Fi for locating.

Device 110 may be configured to obtain a current time from satellite constellation 150, base station 120 or by requesting it from a user, for example. Once device 110 has the current time and an estimate of its location, device 110 may consult a look-up table, for example, to determine a time remaining until sunset or sunrise, for example. Device 110 may likewise gain knowledge of the time of year.

Device 110 may comprise, or be coupled with, at least one sensor, such as, for example, an acceleration sensor, altimeter, moisture sensor, temperature sensor, heart rate (HR) sensor, ambient light sensor, and/or a blood oxygen level sensor. Device 110 may be configured to produce and store, using the at least one sensor, sensor data, for example in a time series that comprises a plurality of samples taken in a time sequence. In some embodiments, device 110 comprises an acceleration sensor and a HR sensor. In some further examples, device 110 comprises an acceleration sensor, a HR sensor and an altimeter.

The acceleration sensor, or motion sensor, may comprise e.g. a 6 degrees of freedom (DoF), or 9 DoF inertial measurement unit (IMU). The acceleration sensor may comprise e.g. a 3D digital accelerometer and/or a 3D digital gyroscope. A full-scale acceleration range of ±2/±4/±8/±16 g and an angular rate range of ±125/±250/±500/±1000/±2000/±4000 degrees per second (dps) may be supported. The acceleration sensor may comprise a 3D magnetometer, for example.

Measurement of the heart rate may be electrical or optical. Electrical measurement is based on electrocardiography sensors worn on a chest strap. Optical measurement is based on photoplethysmography (PPG) sensors which emit light from light emitting diodes through the skin, e.g. on a wrist, and measure how the light scatters off the blood vessels under the skin.

When a user is wearing the wearable device, information may be shown on a display of the wearable device. Information and/or functionality may be provided to the wearable device by a third party. The third party may be a service provider or a company providing training guidance, navigation information, nutrition information, workout tips, tourist information and/or news, for example.

Moments when the information is shown on the display, and/or when a certain action is performed by the wearable device, may be defined based on detected events acting as triggering events. When a triggering event has been detected, information from a third party is provided for display and/or an action defined by the third party is performed by the wearable device. The display format or a display template structure on how the information is shown may be specified beforehand. For example, the template structure may be determined by manufacturer of the wearable device. The triggering events may be defined in terms of sensor data produced by the wearable device using the at least one sensor comprised in the wearable device. A data structure defining the triggering events may be known as a recipe.

Figure 2:
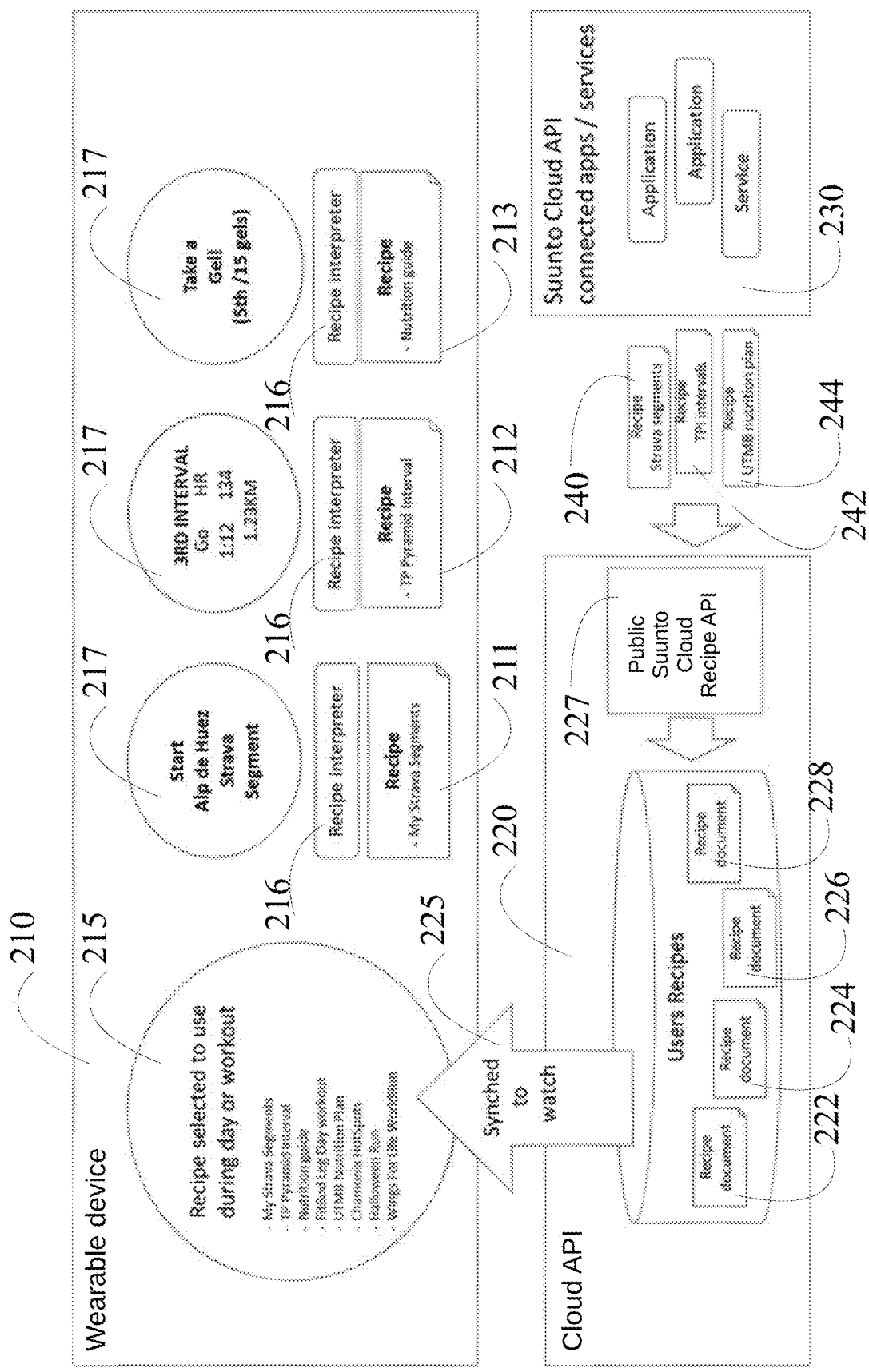
FIG. 2 shows, by way of example, an overview of a system for providing content and/or functional features to a wearable device.

FIG. 2 shows, by way of example, an overview of a system 200 for providing content and/or functional features to a wearable device. For example, a third party may provide content to be displayed on the display of the wearable device, and/or functional features to be performed by the wearable device, during daily use of the wearable device and/or during workout.

The system comprises a wearable device 210. The wearable device may be e.g. the smart watch 110 of FIG. 1. The wearable device comprises at least one memory configured to store at least one recipe. The user may select a recipe for use during workout and/or daily use. For example, the user may select, prior to workout, a recipe by providing user input. The wearable device may receive user input via user interface, e.g. via touch screen or button(s). The recipe may comprise, for example, a city guide or a training session. Selection of recipes 215 may comprise, for example, "My Strava Segments", "TP Pyramid Interval", "Nutrition guide", "FitBod Leg Day workout", "UTMB (Ultra-Trail du Mont Blanc) Nutrition plan", "Chamonix HotSpots", "Halloween run", and "Wings For Life WorldRun".

Content for the recipe may be created by third parties which are external sources creating and providing content to be displayed on the display of the wearable device responsive to triggering events, and/or providing other features for the wearable device such as actions to be performed by the wearable device responsive to triggering events.

Creation of the content for the recipe is based on a format that is specified beforehand. For example, manufacturer of the wearable device may specify the format, that is, the recipe format. The recipe format may be considered as a data format or a data structure that defines what is shown on the display of the wearable device and when, and/or what actions the wearable device is configured to perform and when. For example, the data structure may be a table comprising columns and rows, or a comma-separated values (csv) file, or a character-separated values file. The data structure may comprise headings indicating to the third party which kind of data and/or content the third party may or should include to the data structure. The data structure filled by the third party may be considered as a recipe. In at least some embodiments, the recipe is not an executable binary. In at least some embodiments, the recipe does not include executable instructions written in a programming or scripting language. The recipe may be or comprise a data file or a text file. In at least some embodiments, the recipe is a data file that does not comprise instructions or code to be executed. The recipe provides input elements or parameters for a computer program code or instructions, the computer program code or instructions being stored in at least one memory of the wearable device and executed by at least one processor in the wearable device.

The recipe(s) 222, 224, 226, 228 may be stored in a cloud application programming interface (cloud API) 220. From the cloud API, the recipes may be transmitted or synched 225 to the wearable device, for example via a push message. The cloud API 220 may comprise a public repository of recipes 227, and store accounts of different users, wherein the user may have stored recipes.

The recipe may define metadata of the recipe, such as name of the recipe, a short description of the recipe, whether the recipe is for workout sessions and/or for daily use, during which sport activity the recipe is to be used, etc.

A recipe may define how the wearable device is to act responsive to the recipe. The recipe may define whether the triggering mechanisms or triggering events are based on time (clock time), measured time (duration of workout), measured distance, location, altitude, heart rate and/or some other parameter relating to physiology of the user, speed, pace, detected motion, and/or temperature, for example. In addition, the triggering event may be based on input provided by the user. For example, the user may push a button as a triggering event. As a further example, the wearable device may receive input from an external sensor or device. For example, a cycling power meter may be in communication connection with the wearable device, and the triggering event may be based on input received from this external sensor or device. Examples of external sensors or devices configured to provide input to the wearable device are described in the context of FIG. 9.

For example, if the triggering event is based on measured time, first content may be shown when duration of an exercise is between 5 min to 10 min, and second content may be shown when duration of the exercise is between 10 min to 15 min.

As another example, if the triggering event is based on distance, content may be shown for 5 seconds at following milestones of an exercise: 10 km, 15 km, 25 km.

As a further example, if the triggering event is based on location, content may be shown for 20 seconds when within certain range of latitude and longitude coordinates.

As a further example, the triggering event may be based on measurements of different quantities and logical steps. For example, the triggering event may be based on heart rate, time, and/or speed. For example, a first screen X may be shown as long as heart rate is below 150 bpm (beats per minute), a second screen Y may be shown for next 10 min after heart rate exceeds the threshold of 150 bpm, and a third screen X may be shown as long as speed is below 10 km/h. The logic may be defined by the third party service. For example, it may be defined that if heart rate is below 70% of the max heart rate of the user, text "OK" may be displayed, and if heart rate is above that limit, text "Hard" may be displayed.

As a further example, triggering events may be defined as delta values, that is, based on a difference to a value associated with previous triggering event. For example, referring to an example above, the triggering events based on distance may be alternatively defined as: 10 km, $\Delta 5$, $\Delta 10$, which would be equivalent to 10 km, 15 km, 25 km. As another example, the user may be instructed to recover after a first interval until heart rate is below a certain value. The following triggering event may be defined as $\Delta 5$ min with text "$2^{nd}$ interval", meaning that from a time point wherein the heart rate has been detected to be below a certain value, the following 5 min would be an interval. Thus, the triggering events may be based on measurements of different quantities in the same recipe.

Two or more recipes may be used in parallel. For example, one recipe may comprise triggering events that are based on location and another recipe may comprise triggering events that are based on time.

The wearable device may comprise an interpreter 216 or a parser configured to interpret, or parse, the recipe and its content. The wearable device is configured to, using the interpreter, read and interpret the recipe and use the information in the recipe in order to perform actions according to the recipe. The recipe may be interpreted by the wearable device when an exercise is ongoing and/or during daily use. Action to be performed by the wearable device may comprise, for example, displaying certain content specified in the recipe, activating an alarm, etc. The interpreter triggers actions according to the triggering events defined in the recipe. The interpreter may be part of the firmware of the wearable device, for example. The interpreter comprises or has access to a computer program instructions or code stored in a memory of the wearable device. The recipe provides input elements or parameters for those computer program instructions. The wearable device comprises at least one processor or processor core which is configured to execute the computer program instructions to cause the wearable device to perform actions. The computer program instructions use the input elements provided by the recipe. In at least some embodiments, the recipe does not include executable instructions written in a programming or scripting language. The recipe may be or comprise a data file or a text file. The input provided by the recipe for the computer program instructions stored in the wearable device may comprise at least one or more triggering events, one or more display templates, and one or more content elements.

A recipe may define the content elements, that is, what content is shown on the display, and how the content is shown on the display, in response to detecting a triggering event. For example, the display may be divided into fields that may show different content at the same time. For example, the recipe may define that the display uses four fields and shows the following parameters during a workout: heart rate, speed, pace, location based on GPS. As another example, the recipe may define that display uses one field and shows text such as "Next 20 seconds jumping jacks" or "Good job!".

For example, the content to be shown may comprise image content. Image content may be provided by a third party service, and may be e.g. a picture of a person making squats, or a nutrition icon with carbohydrate drink.

A display view or a display template may be defined as part of the recipe. The display template may be e.g. a graph, a text field, or a field comprising two (2), three (3), four (4), five (5) fields, for example, or a table. The display template may be defined by the manufacturer of the wearable device. The third party service may define in the recipe what kind of a display view or template is used and when. A recipe may define, how information derived from sensor data produced internally by the wearable device is displayed on a display of the wearable device. Definition of the display templates as part of the recipe is beneficial especially due to a limited size of the displays of the wearable devices. The display template allows the third party service to determine how the content is displayed on the display. This way, a situation is avoided wherein a third party service tries to fit too much information, e.g. letters and/or numbers, to an area or a field of a display. In other words, the selectable display templates prevent the third party service from providing content to be displayed on an area, which is too small for the content to be displayed. It depends on the content, what kind of a template is suitable such that the content still fits nicely on the display of the wearable device.

A recipe, e.g. a first recipe, may comprise indication of a second recipe. This indication may be defined in an action corresponding to a triggering event. The interpreter detects the second recipe and is configured to then interpret the second recipe, and return to the first recipe to continue the first recipe once the second recipe is complete. For example, the recipe may comprise an address, e.g. uniform resource locator (URL), wherein the second recipe may reside. In case the interpreter or parser detects a second recipe comprised in a first recipe, the wearable device may be configured to download the second recipe to a memory of the wearable device to have the second recipe ready to be run when triggered. Alternatively, the wearable device may prompt the user so that the user may provide input on whether the second recipe is to be downloaded beforehand or when the recipe is triggered.

For example, the first recipe is started at home of the user when the user starts jogging. The first recipe comprises a second recipe, and the user may select whether the second recipe is to be downloaded at home or when the second recipe is triggered. The user selects that the recipe is to be downloaded when triggered. The first recipe may comprise a triggering event based on location of a sport center. The user arrives at the sport center. This location may trigger a second recipe comprising a workout session suitable for the sport center. The second recipe may be downloaded to the wearable device in response to detection of the triggering event, that is, the location of the sport center. The user may use wireless network provided by the sport center for downloading, for example.

For example, the user has selected a recipe called "My Strava Segments" 211. The recipe interpreter 216 may interpret the recipe and based on the interpretation, the display 217 of the wearable device may show on a text field "Start Alp de Huez Strava Segment" when a certain triggering event, defined in the recipe, has been detected. The triggering event may be based on location, for example. FIG. 4 shows a more detailed example of a recipe relating to Strava Segments.

Figure 3:
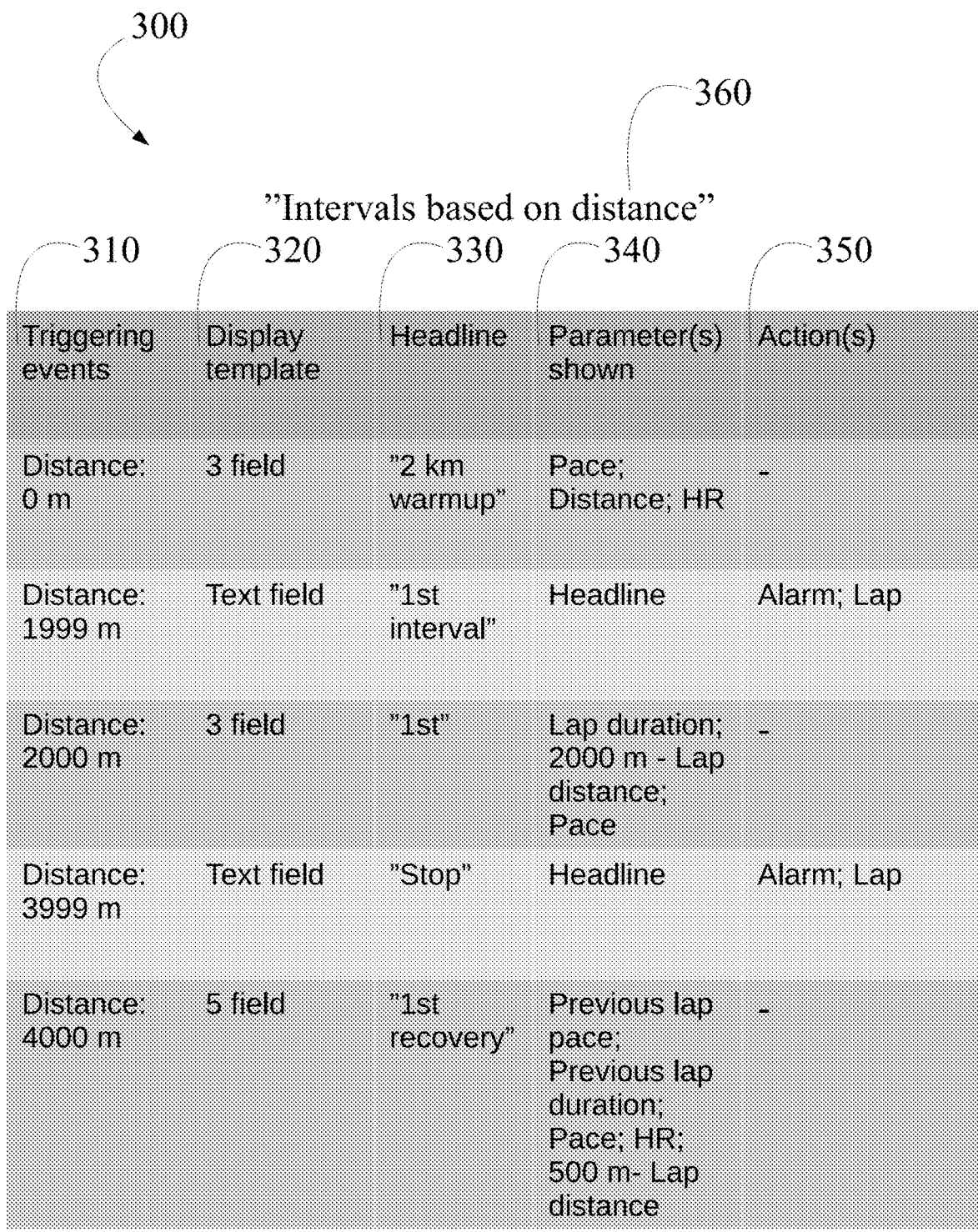
FIG. 3 shows, by way of example, a recipe.

As another example, the user has selected a recipe called "TP Pyramid interval" 212. The recipe interpreter 216 may interpret the recipe and based on the interpretation, the display 217 of the wearable device may show a heading "$3^{rd}$ interval" and on a template of three fields the following parameters: time left or time to go 1:12 min; HR 134; distance 1.23 km, when a certain triggering event has been detected. The triggering event may be based on duration of the workout, for example. FIG. 3 shows a more detailed example of a recipe relating to intervals.

As a further example, the user has selected a recipe called "Nutrition guide" 213. The recipe interpreter 216 may interpret the recipe and based on the interpretation, the display 217 of the wearable device may show on a text field "Take a Gel!", and on another field "($5^{th}$/15 gels), when a certain triggering event has been detected. The triggering events may be based on duration of the workout. The recipe may define that a nutrition gel is to be taken every 30 min of an ultramarathon, and to indicate that, the instruction "Take a gel!" is displayed on the display. The recipe may further define additional text to be shown every 30 min, that is, "$1^{st}$/15 gels", "$2^{nd}$/15 gels", "$3^{rd}$/15 gels", etc.

A cloud API for recipes may be considered as a model where a third party 230 may push recipes 240, 242, 244 to the cloud API 220, from which the recipes may be synched 225 to the wearable device 210. The wearable device 210 may download the recipes from the cloud API. Third parties 230 may be services and/or applications connected to the cloud API 220. Third party may be a service provider or a company providing training guidance, navigation information, nutrition information, workout tips, tourist information and/or news, for example. For example, training planning tool may push an interval workout as a recipe to be synched to the wearable device. The content and/or functionality may be provided according to a data structure or the recipe format defined by the manufacturer of the wearable device. Alternatively, the cloud API 220 may fetch the content for the recipes from a source of a third party 230, such as API of the third party, and the content may be converted into the recipe format by the cloud API 220.

The user may have a number of recipes stored in one's account. The number of recipes may be limited. For example, the user may have maximum 100 recipes in one's account. The recipes stored in user account may be automatically synched to the wearable device. When the user selects a recipe for workout, the recipe is available in the wearable device. This means that the recipe is available before a workout session is started, for example.

FIG. 3 shows, by way of example, a recipe 300. The recipe format may define, for example, the following properties of the recipe:

When the content is shown, that is, the triggering events 310: The triggering events may be based on time, distance, location, heart rate, etc., or a combination of these.

Display type or template 320: Does the display show text on a text field, different parameters on three field view, or different parameters on five field view? The number of fields may be e.g. 1, 2, 3, 4, 5, 6, depending on the wearable device.

Headline 330: Headline may be text or an icon, for example. If the text field is used, the headline text may define the text that is to be displayed on the text field.

Parameter(s) shown 340: What parameters are shown on different fields on the display? The number of provided parameters may correspond to the number of fields defined by the display template 320.

Action(s) 350: In addition to displaying different content, the triggering events may trigger other actions. For example, an alarm may be triggered in the beginning of and after each lap, and/or a virtual push of a lap button may be triggered. That is, the lap may be configured to start and/or end. The laps are visible in stored workout data, and the user may afterwards analyse the workout session and compare the laps. As a further example, an action may be such that the wearable device is configured to store data in a memory. For example, a question may be posed to a user, in response to the corresponding triggering event 310, on a display of the wearable device, whether the user wants to store data such as lap times. If the user provides input in order to store data, the wearable device stores data on a workout session to a memory of the wearable device or to a cloud memory.

Alternatively, the wearable device may, by default, store the data on the workout session without asking from the user. The data to be stored in response to a triggering event may be defined in the recipe. The data may comprise data of a current state or status of the wearable device, such as current location, battery level, time, context data, etc. Context data may be considered to comprise, for example, weather, location, time, etc. Actions 350 are optional in the sense that in some embodiments, actions 350 are absent.

Gauge that shows graphically e.g. a measurement value. For example, maximum HR of a user may be pre-set and shown as a 100% or full scale value, and the gauge may indicate the current HR as a percentage of the maximum HR. For example, the gauge may indicate the current HR as 40% or $4/10$ of the full scale. The graphical indicator may be e.g. a pointer or a bar.

A third party may have provided content for the recipe 300. For example, the third party may have filled a table with triggering events, and corresponding display template, headline, parameters, and actions.

The user may select a recipe 300 for workout having a title 360: "Intervals based on distance". The title 360 may be part of the recipe, for example title 360 may be comprised in metadata of the recipe. The triggering events 310 are, in the example of FIG. 3, based on distance. The user starts the workout, and the distance is 0 m. This means that the first triggering event is detected. According to the recipe, the display uses three field view in the beginning of the workout. Headline is defined as "2 km warmup". During the warmup, the display shows following parameters: pace, distance, heart rate.

When the user has run 1999 m, the second triggering event is detected. The display uses the text field showing "$1^{st}$ interval". Alarm is also triggered, since the warmup period is over and the first interval or lap begins. Alarm may be, for example, a sound and/or a light on a display, or the wearable device may vibrate for a short time. A lap button may be virtually pushed as a sign of beginning of a lap.

The third triggering event is 2000 m. The display uses the field view during the $1^{st}$ interval. Display shows "$1^{st}$" on the headline. In the three fields, the display shows lap duration, "2000 m—lap distance", and pace. The parameter "2000 m—lap distance" may be calculated by the wearable device. The 2000 m is the length of the interval, and the lap distance may be determined based on GPS signal, for example.

The fourth triggering event is 3999 m, that is, when the user has finished, or almost finished, the first interval. The display uses the text field showing "Stop". Alarm is also triggered, since the first interval or lap is over. A lap button may be virtually pushed as a sign of the end of the lap.

The fifth triggering event is 4000 m. The display uses five field view, and the headline is defined as "$1^{st}$ recovery". In the five fields, the display shows previous lap pace, previous lap duration, current pace, current heart rate, "500 m—lap distance". The parameter "500 m—lap distance" may be calculated by the wearable device. The 500 m is the length of the recovery period, and the lap distance may be determined based on GPS signal, for example.

The sixth triggering event may be 4500 m, that is, when the user has finished the recovery period. Triggering event may have an additional condition. For example, it may be defined that the recovery lap is at least 500 m, and the heart rate needs to be below a certain value. When these both conditions are fulfilled, the recovery period may be set as finished, and the $2^{nd}$ interval may start.

As another example of a workout recipe, let us consider a crossfit application "Daily Tabata session" provided by a third party service. The third party service may create each day a new workout session and push that to the cloud API in a recipe format defined by the manufacturer of a wearable device. For example, the third party may create a recipe "Wednesday Tabata session". The wearable device may be synched with the cloud API such that the wearable device retrieves the recipe from the cloud. The user may be a user of a crossfit app "Daily Tabata session". User may select the recipe "Wednesday Tabata session" prior starting the workout. In the beginning, the display has been defined to use a three field view with duration of the workout, current heart rate, and text field. In the beginning, the text field may show text "warmup". After 10 minutes of warmup, the display view may change to a text field with text "Squats" for 20 seconds. After the first 20 seconds of squats, 10 seconds of rest follows. During the 10 seconds, the text field may show "Rest". Then, an alarm may be activated and a view with a 40 seconds countdown timer may be displayed during which a text "Squats" is shown on the text field. After the 40 seconds of squats, 10 seconds of rest follows. After the resting period, the text field shows "Pushups" for 20 seconds. The information with the timing and which text to show is provided by the third party service.

FIG. 4 shows, by way of example, a recipe 400. A user may select a recipe for workout having a title 460: "Strava segments". Third party has provided content for the recipe 300. For example, the third party has filled a table with triggering events 410, display templates 420, headlines 430, parameters 440 and actions 450.

The triggering events are based on location. Location may be based on GPS signal and coordinates, for example. If the wearable device detects a location according to lateral and longitudinal coordinates defined in the recipe, the triggering event is detected.

First triggering event defines no location. In the beginning of the workout, the display uses three field view, and the fields show speed, distance and duration of the workout. A headline "Strava Segments" is shown on the display.

The second triggering event is defined by coordinates of a location wherein a Strava segment or section starts. The wearable device detects the location, shows text "Start—Alpe d'Huez". The text may be shown for a pre-determined time, e.g. for 5 seconds. Alarm is triggered to indicate start of the segment. Lap button is virtually pushed as a sign of beginning of the lap or segment.

The third triggering event may be defined as a short time period after detection of the start of the segment. In other words, it may be defined that the start of the segment lasts for a short time period, after which the third event starts. The short time period here may be e.g. 4, 5 or 6 seconds. During the Strava segment, the display uses three fields showing "Personal record—lap duration", speed, "segment length—lap distance". Text "Alpe d'Huez" is shown as a headline. If the user is taking the segment for the first time, the average time or the fastest time may be shown instead of the personal record.

The fourth triggering event is defined by coordinates wherein the Strava segment ends. The display uses three fields and shows "Personal record—previous lap duration", previous lap speed, pervious lap average heart rate. Alarm is triggered to indicate end of the segment. Lap button is virtually pushed as a sign of the end of the lap or segment. It may be defined that the end of the segment lasts for a short time period, e.g. 5 seconds. Text "End—Alpe d'Huez" is shown as a headline.

The workout may continue until the wearable device detects another Strava segment based on coordinates, or the user stops the workout. During the workout, the wearable device may be configured to show on the display, for example, speed, distance and duration, as before the first detected Strava segment.

Figure 5:
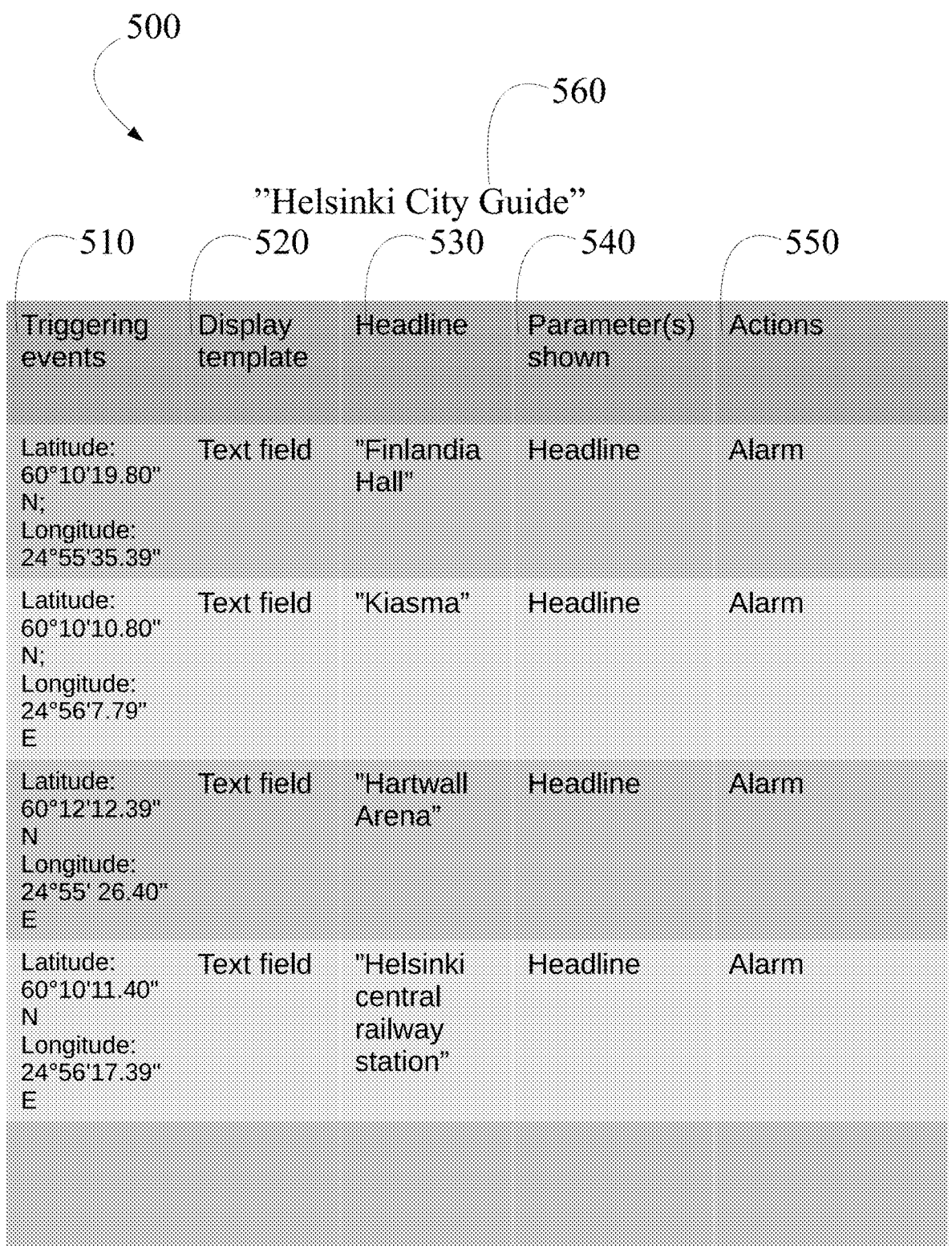
FIG. 5 shows, by way of example, a recipe.

FIG. 5 shows, by way of example, a recipe 500. A user may select a recipe having a title 560 "Helsinki City Guide". Third party has provided content for the recipe 500. For example, the third party has filled a table with triggering events 510, display templates 520, headlines 530, parameters 540, and actions 550.

The triggering events are based on location, i.e. based on latitude and longitude GPS coordinates. The display uses text field. When the user is moving around the city, and when the user passes by or the location of the user is close enough to the specified coordinates, a certain text will be shown on the display. Location being close enough to the specified coordinates may be determined as a distance range from the coordinates. For example, when the user is within 50 m from the specified coordinates, the user may be considered to be close enough. The triggering events that are based on location may be in a predefined order or in a random order. If the triggering events are in a predefined order, the user may follow a predefined path, and the wearable device tries to detect a location corresponding to a next triggering event. If the triggering events are in a random order, the wearable device may scan the triggering events and when passing a location or being close enough to a location corresponding to any of the triggering events, the wearable device detects the triggering event.

For example, when the user passes by or is close enough to following coordinates: Latitude: 60° 10'19.80"N; Longitude: 24° 55'35.39"E, the text "Finlandia Hall" is displayed. The text may be displayed for a pre-determined time or it may be displayed as long as the user is located close enough to the coordinates in question. In addition, an alarm may be activated. When the user is close enough to following coordinates: Latitude: 60° 10'10.80"N; Longitude: 24° 56'7.79"E, the text "Kiasma" is displayed. When the user is close enough to the following coordinates: Latitude: 60° 12'12.39"N Longitude: 24° 55'26.40"E, the text "Hartwall Arena" is displayed. When the user is close enough to the following coordinates: Latitude: 60° 10'11.40"N Longitude: 24° 56'17.39"E, the text "Helsinki central railway station" is displayed.

As another example of a city guide, let us consider a guide "Run in Manhattan". The third party service offering city guide tools may push the guide into the cloud API in the recipe format defined by the manufacturer of the wearable device. The recipe is then synched to the wearable device. The user may select the recipe "Run in Manhattan" prior starting the workout. Each time the user is close enough or passes a location defined by the recipe, the display of the wearable device may show a view defined in the recipe. For example, the view may be shown for a predetermined time, e.g. 30 seconds, or as long as the user is close to the location. The content on the display may comprise e.g. a name of the location and an image or picture of an attraction at that location. For example, "Empire state building" and a corresponding image may be shown on the display of the wearable device.

Figure 6:
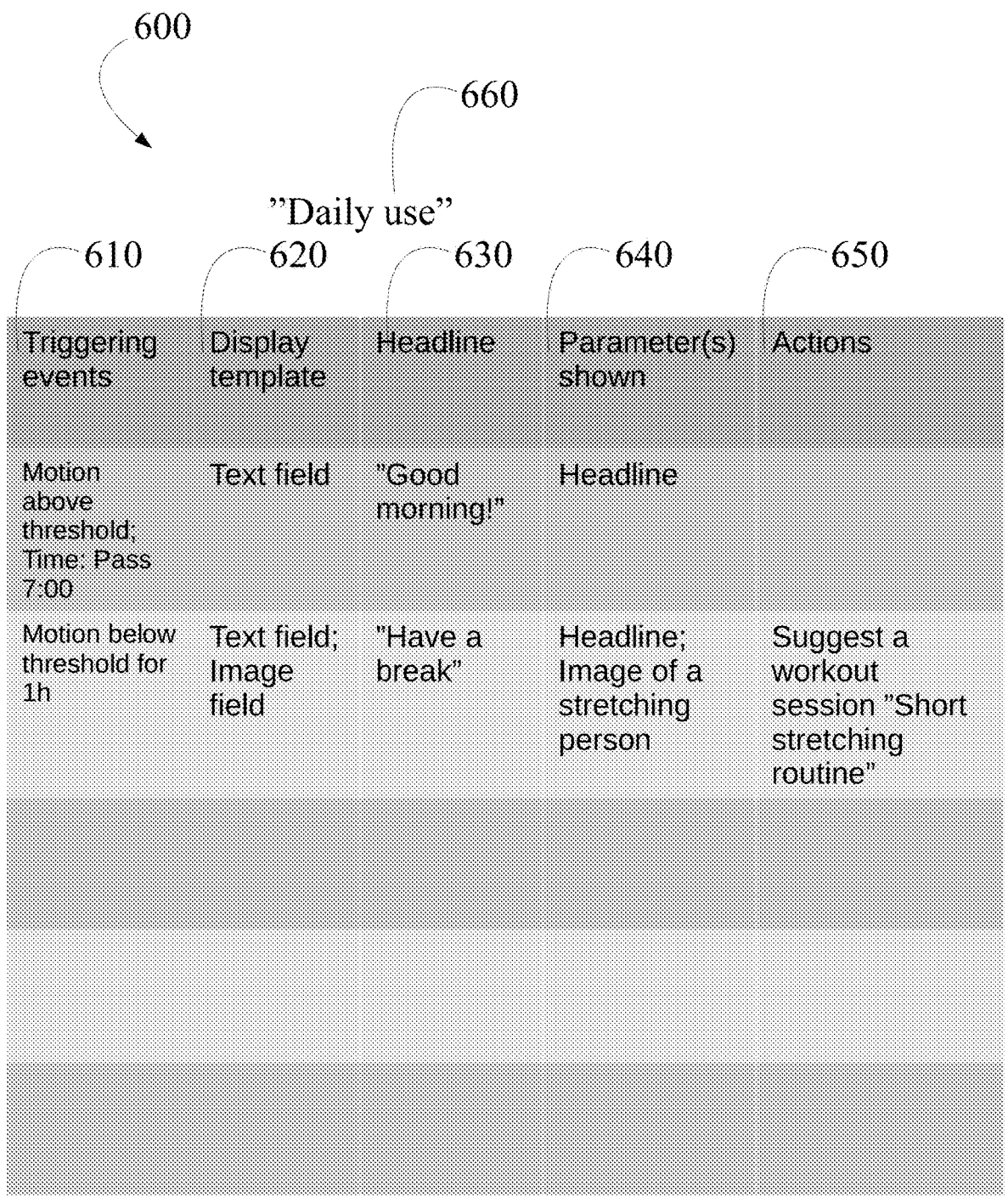
FIG. 6 shows, by way of example, a recipe.

FIG. 6 shows, by way of example, a recipe for daily use. A triggering event may be based on detected motion. For example, the wearable device comprises a motion sensor. When a user of the wearable device is sleeping, motion detected by the motion sensor is minimal. When the user wakes up from the bed, increased motion is detected by the motion sensor. For example, the motion detected is above a predetermined threshold. The wearable device may also use the clock time and determine that it is a normal time for the user to wake up. When it is detected that the user has woken up, based on the detected motion and that the time is pass 7:00, the display may show text "Good morning!".

The second triggering event may be based on detecting that the motion has been below a predetermined threshold for a predetermined time, e.g. 1 h. The user may be working and sitting in front of a computer. Then, the display may show a text "Have a break" and an image of a stretching person. Action may be triggered for the wearable device which is configured to prompt to a user a suggestion to start a workout session "Short stretching routine". If the user provides input to start the workout session, the wearable device may retrieve the workout session from a memory of the wearable device or from a cloud. The workout session may comprise instructions for the stretching that may be displayed on the display of the wearable device. Instructions may comprise images, text, audio and/or videos. For example, a video may be streamed to a wearable device.

As described above, two or more recipes may be used in parallel. For example, recipe for daily use may be used during the whole day, and at some time point during the day, the user may select a recipe for a workout to be used. The recipe for daily use may continue to run on the background. After the workout, the recipe for daily use which has been running on the background will continue. The recipe for daily use may comprise the recipe for a workout as an action corresponding to a triggering event which is a certain time, for example.

Figure 7:
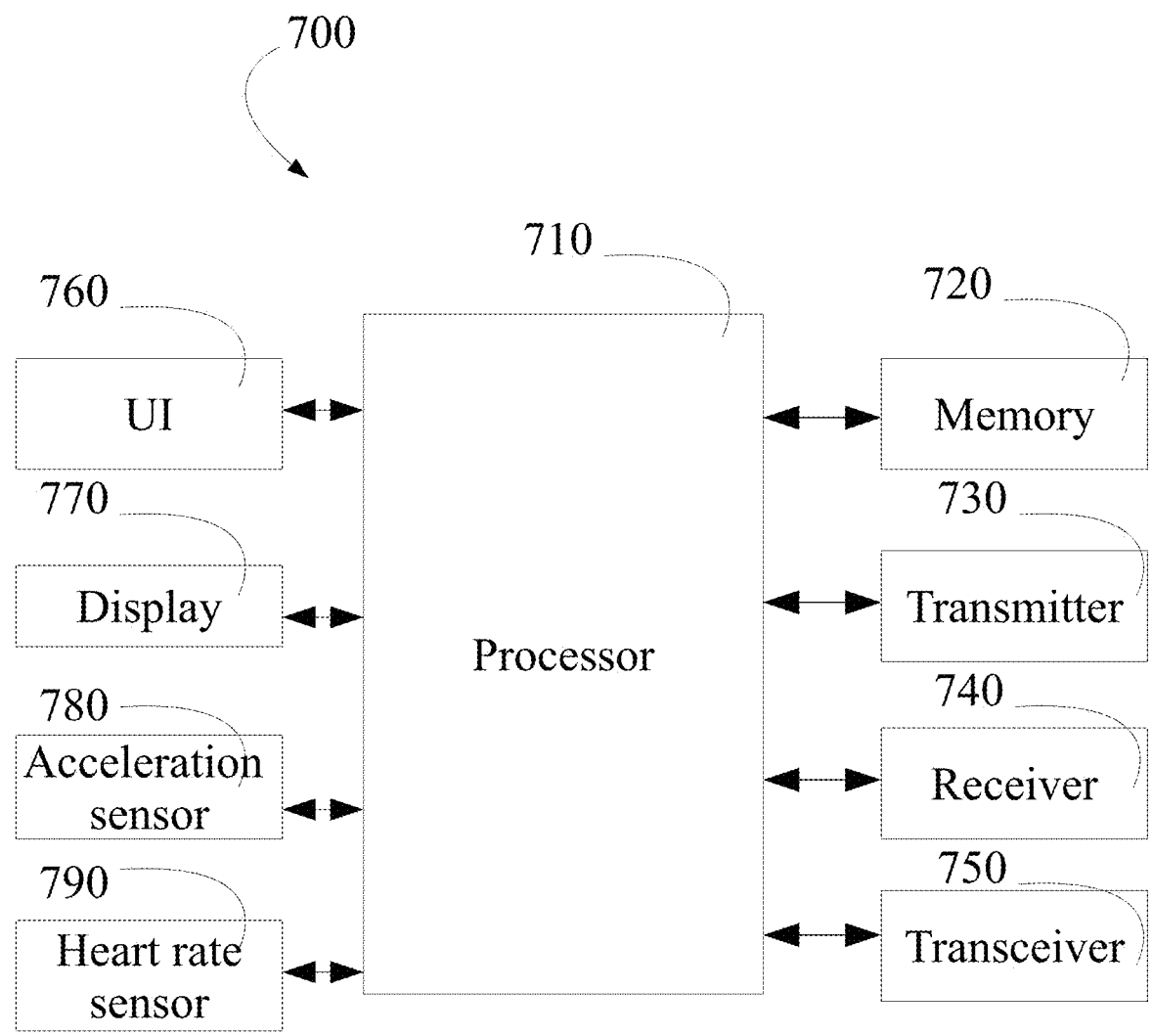
FIG. 7 shows, by way of example, a block diagram of a wearable device.

FIG. 7 shows, by way of example, a block diagram of a wearable device. FIG. 7 shows, by way of example, a block diagram of an apparatus. Illustrated is device 700, which may comprise, for example, a wearable device such as a sport watch or smart watch 110 of FIG. 1. Comprised in device 700 is processor 710, which may comprise, for example, a single- or multi-core processor wherein a single-core processor comprises one processing core and a multi-core processor comprises more than one processing core. Processor 710 may comprise, in general, a control device. Processor 710 may comprise more than one processor. Processor 710 may be a control device. A processing core may comprise, for example, a Cortex-A8 processing core manufactured by ARM Holdings or a Steamroller processing core designed by Advanced Micro Devices Corporation. Processor 710 may comprise at least one Qualcomm Snapdragon and/or Intel Atom processor. Processor 710 may comprise at least one application-specific integrated circuit, ASIC. Processor 710 may comprise at least one field-programmable gate array, FPGA. Processor 710 may be means for performing method steps in device 700. Processor 710 may be configured, at least in part by computer instructions, to perform actions.

Device 700 may comprise memory 720. Memory 720 may comprise random-access memory and/or permanent memory. Memory 720 may comprise at least one RAM chip. Memory 720 may comprise solid-state, magnetic, optical and/or holographic memory, for example. Memory 720 may be at least in part accessible to processor 710. Memory 720 may be at least in part comprised in processor 710. Memory 720 may be means for storing information. Memory 720 may comprise computer instructions that processor 710 is configured to execute. When computer instructions configured to cause processor 710 to perform certain actions are stored in memory 720, and device 700 overall is configured to run under the direction of processor 710 using computer instructions from memory 720, processor 710 and/or its at least one processing core may be considered to be configured to perform said certain actions. Memory 720 may be at least in part comprised in processor 710. Memory 720 may be at least in part external to device 700 but accessible to device 700. Memory 720 may store one or more recipes provided by a third party.

Device 700 may comprise a transmitter 730. Device 700 may comprise a receiver 740. Transmitter 730 and receiver 740 may be configured to transmit and receive, respectively, information in accordance with at least one cellular or non-cellular standard. Transmitter 730 may comprise more than one transmitter. Receiver 740 may comprise more than one receiver. Transmitter 730 and/or receiver 740 may be configured to operate in accordance with global system for mobile communication, GSM, wideband code division multiple access, WCDMA, 5G, long term evolution, LTE, IS-95, wireless local area network, WLAN, Ethernet and/or worldwide interoperability for microwave access, WiMAX, standards, for example.

Device 700 may comprise a near-field communication, NFC, transceiver 750. NFC transceiver 750 may support at least one NFC technology, such as NFC, Bluetooth, Wibree or similar technologies.

Device 700 may comprise a port for a cable for wired data communication or charging. For example, the device may comprise a USB port.

Device 700 may receive one or more recipes from an external source using the receiver 740 and/or the transceiver 750, for example. Device may receive satellite positioning information using the receiver 740.

Device 700 may comprise user interface, UI, 760. UI 760 may comprise at least one of a display, buttons, a keyboard, a touchscreen, a vibrator arranged to signal to a user by causing device 700 to vibrate, a speaker and a microphone. A user may be able to operate device 700 via UI 760, for example to select a recipe and/or start and/or stop a workout session, to manage digital files stored in memory 720 or on a cloud accessible via transmitter 730 and receiver 740, or via NFC transceiver 750.

Device 700 may comprise, or may be coupled to, a display 770. The display may be operated by the processor(s). For example, the display may be configured to show, in response to detecting a triggering event, one or more content elements corresponding to the triggering event according to a display template corresponding to the triggering event.

Device 700 may comprise sensors, such as an acceleration sensor 780, heart rate sensor 790, altimeter, moisture sensor, temperature sensor, ambient light sensor, and/or a blood oxygen level sensor.

Figure 8:
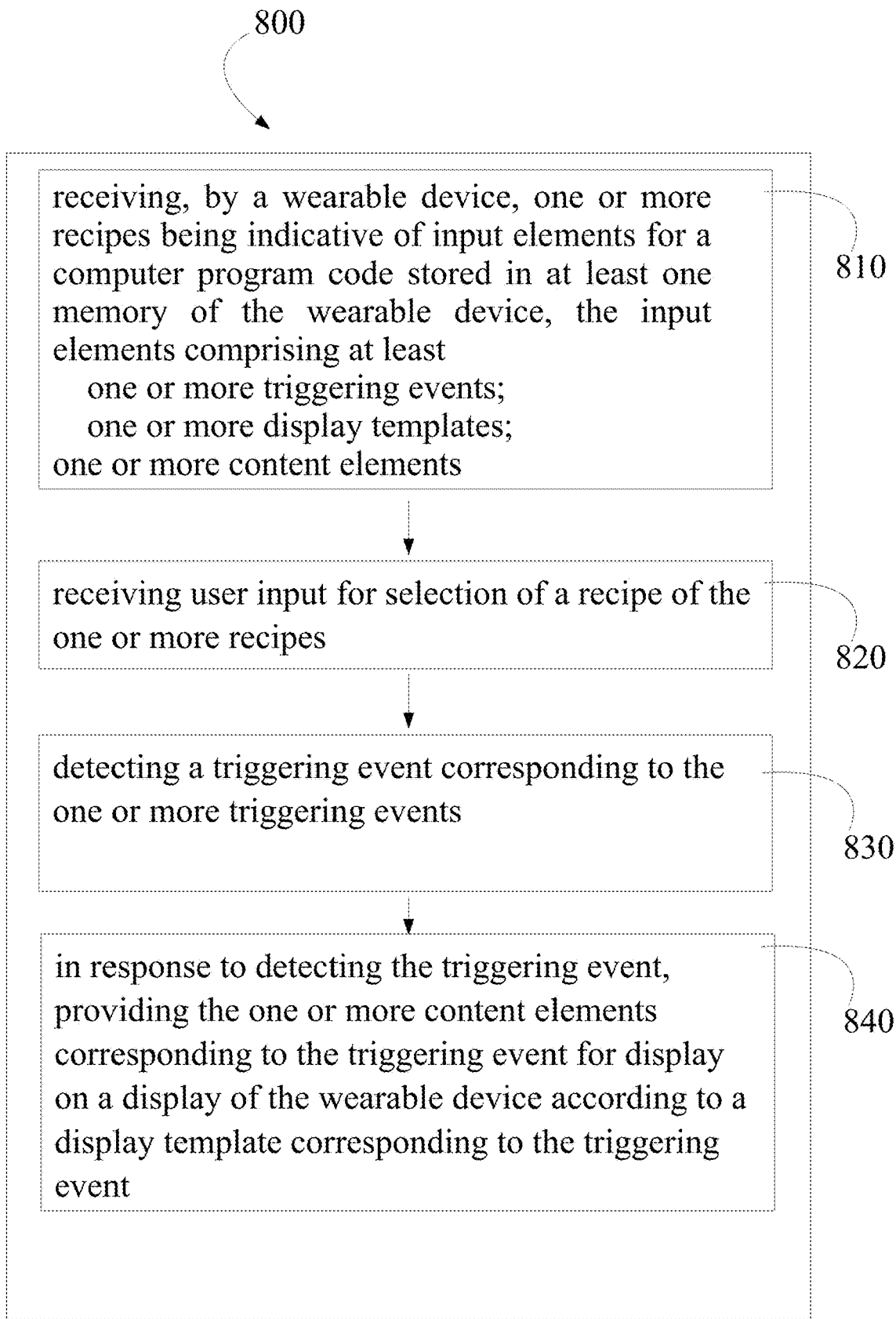
FIG. 8 shows, by way of example, a flowchart of a method.

FIG. 8 shows, by way of example, a flowchart of a method. The method 800 comprises receiving 810, by a wearable device, one or more recipes being indicative of input elements for a computer program code stored in at least one memory of the wearable device, the input elements comprising at least one or more triggering events; one or more display templates; and one or more content elements. The method 800 comprises receiving 820 user input for selection of a recipe of the one or more recipes. The method 800 comprises detecting 830 a triggering event corresponding to the one or more triggering events. The method comprises in response to detecting the triggering event, providing 840 the one or more content elements corresponding to the triggering event for display on a display of the wearable device according to a display template corresponding to the triggering event.

The computer code or program instructions that cause the method to be performed, when executed by at least one processor in a wearable device, may comprise the computer code for which the input elements are received as a subprogram, for example.

The recipe model as disclosed herein is beneficial for third party services to have their features available in wearable devices in real time and without application development or software development by the third party services themselves. The third party services do not need to know how to do software development which may be challenging for specific devices such as wearable devices. User may have new features to the wearable device without software updates. The wearable device may receive the recipes with new features or content via synchronization operation with the cloud API. The wearable device might not need auxiliary applications installed, but it is the recipe that enables functionality of the device according to features provided by third party service.

Figure 9:
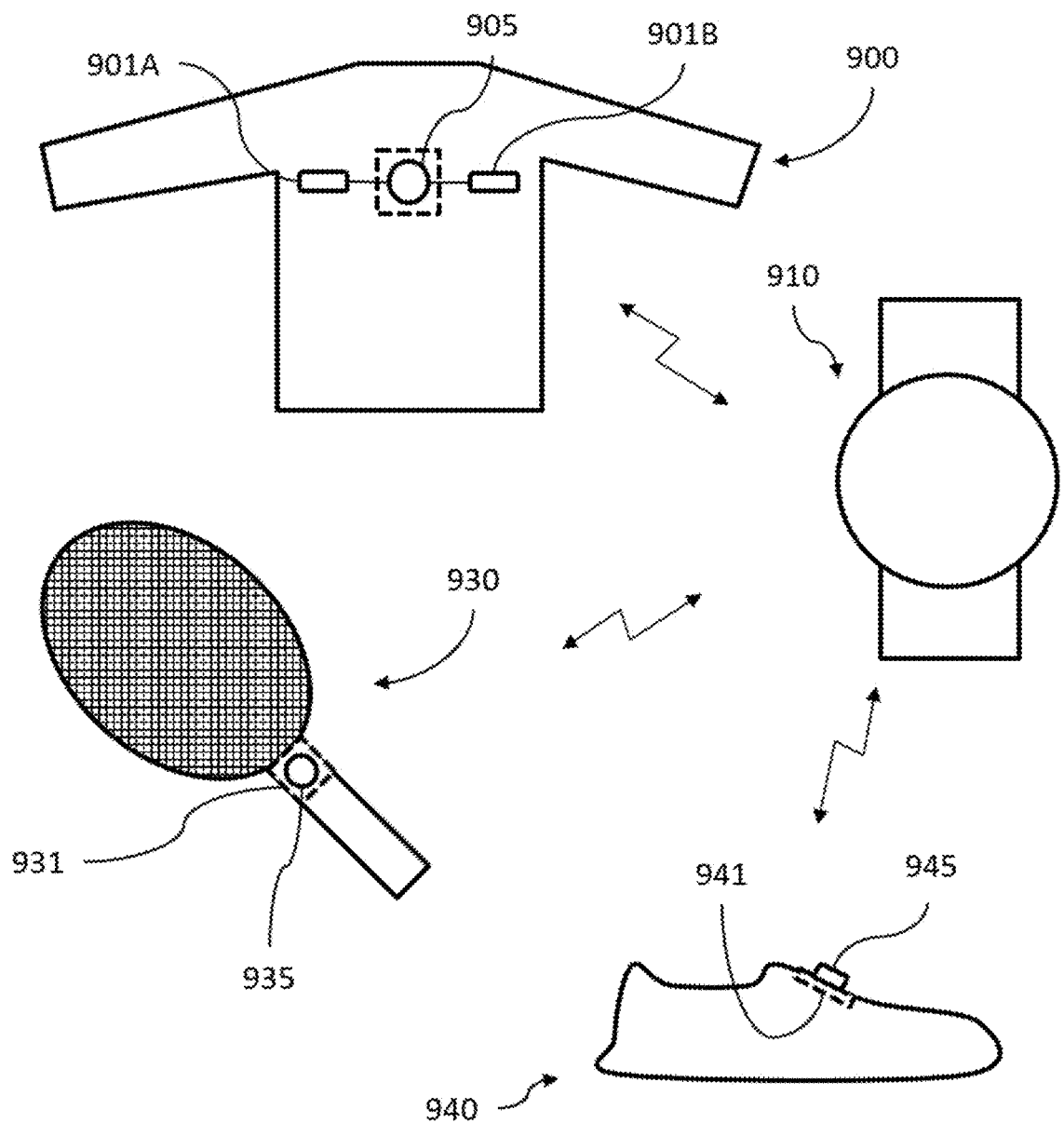
FIG. 9 shows, by way of example, external sensors and/or devices communicating with a wearable device.

FIG. 9 shows, by way of example, external sensors and/or devices communicating with a wearable device. As described, the triggering event may be based on input received from an external sensor or device. The wearable device 910 may be a central unit or a monitoring unit, which communicate with one or more external sensors or devices via a communication connection. These sensors and/or devices form, together with the wearable device, a personal area network (PAN). Communication between the devices may be based on wireless communication technologies, such as Bluetooth or ultra wideband or induction wireless, and/or based on wired communication.

A sports garment, e.g. a shirt 900 or trousers, may comprise electromyography (EMG) pads 901A, 901B mounted in the garment. The EMG pads are coupled with a communication module 905, and the communication module may communicate information provided by the EMG pads to the wearable device 910.

A sport item, e.g. a tennis racket 930, may comprise a communication module 935. Sensors 931, e.g. acceleration sensors, orientation sensors, and/or position sensors, which are mounted on the racket, are coupled with the communication module 935. The communication module may communicate acceleration, orientation and/or position information provided by the sensors to the wearable device 910. For example, the triggering event may be defined as a number of hits which may be calculated based on the sensor information received from the racket.

A further sports garment, e.g. a shoe 940, may comprise a communication module 945. Sensors, 941, e.g. acceleration sensors, orientation sensors, and/or position sensors, which are mounted on the shoe, are coupled with the communication module 945. The communication module may communicate acceleration, orientation and/or position information provided by the sensors to the wearable device 910. The shoe may be equipped with a pedometer.

Examples of pieces of garment, wherein sensors may be mounted, comprise shirts, trousers, socks, hats, caps, footwear, handwear and belts and various pieces of sports equipment necessary for any particular sports, including rackets, bats, clubs, sticks, skis, bicycles, balls, vehicles, and bags.

Examples of sensors comprised in the sports items include the EMG, acceleration, orientation, position sensors already mentioned above, and additionally temperature and pressure sensors, such as air pressure sensors or tactile sensors, and photosensors. Sensor types include, for example, conductive electronic potential sensors, micromechanical acceleration sensors, micromechanical gyroscopic sensors, micromechanical magnetic sensors, micromechanical pressure sensors, satellite positioning system sensors (e.g. GPS or GLONASS) and resistive and capacitive touch sensors (with optional touch position and/or touch force detection capability) and digital imaging sensors (e.g. multipixel CCD or CMOS sensors). Bicycle may be equipped with a chain-tension sensor.

Sports item examples include heartbeat ECG belts, muscular EMG belts or garments and tennis rackets, golf clubs, skiing equipment with acceleration sensors or orientation sensors and photographic devices used during the performance.

At least in some embodiments, the triggering event may be based on a quantity derived from one or more of clock time; measured time; measured distance; location; altitude; heart rate; speed; pace; detected motion; temperature; input from external device; user input. For example, the triggering event may be based on a quantity derived from input received from one or more sensors. Examples are given in the following paragraphs.

For example, triggering event may be based on running speed which may be calculated as explained below. Acceleration values $a_x$, $a_y$ and $a_z$ in three orthogonal directions x, y, z are measured using acceleration sensors. The total magnitude of the acceleration vector is $a_1$:

$$a_1 = \sqrt{a_x^2 + a_y^2 + a_z^2}.$$

Gravity $g_0$ is subtracted from total acceleration, yielding movement-related acceleration $a_2$:

$$a_2 = a_1 - g_0.$$

A plurality of movement-related acceleration values $a_2$ are measured over a time period $\Delta t$ and used to calculate average movement acceleration $a_{ave}$ $$a_{ave} = \frac{\sum a_2(t)}{\Delta t}.$$

Then, the average acceleration $a_{ave}$ is converted to running speed $v_{running}$ using a piecewise linear function $f_{mapping}(\ )$, also applying a cadence check function $f_{cadenceCheck}(\ )$, which checks that $a_{ave}$ and cadence detected from the acceleration signal are at allowed ranges:

$$v_{running} = f_{cadenceCheck}(cadence, a_{ave}) f_{mapping}(a_{ave}).$$

The mapping function $f_{mapping}(\ )$ can have a predefined form, but its form can also be changed using reference measurements to adapt the function to individual running characteristics of the person.

The triggering event may be based on estimation of a recovery pulse. The recovery pulse may be recursively estimated on the basis of current pulse by using the resting pulse and the maximum pulse of a person as pre-data. These parameters can be typically entered into the apparatus by the user or the apparatus can define them automatically by means of a software application. In the present calculation the resting pulse can be constant regardless of the person, e.g. 60 bpm, which is a good average estimate. The method proceeds by steps as follows:

1. The pulse (HR) is measured and it is converted into a percentage of the pulse reserve: $hrr_{now} = (HR - HR_{rest}) * 100\% / (HR_{max} - HR_{rest})$ 2. The saturation level ($hrr_{s1}$) of the current pulse level ($hrr_{now}$) is read from a table, the saturation level being also the pulse reserve percentage in unit.

3. The current recovery pulse level ($hrr_{recovery\_old}$) is updated towards the saturation level by means of a saturation coefficient ($sl_{coeff}$) read from the table for producing a new recovery pulse level ($hrr_{recovery\_new}$). The update equation can be e.g. of the form $hrr_{recovery\_new} = hrr_{recovery\_old} + sl_{coeff} * (hrr_{s1} - hrr_{recovery\_old})$.

The triggering event may be based on calculated recovery time. The recovery pulse calculation may be used for calculating recovery time. The recovery time depends on the duration of the exercise and its load. In practice the recovery time can be estimated by calculating the effective exercise time connecting all these factors. Thus the measured pulse is put in relation with the maximum performance pulse $HR_{maxperf}$ relating to the duration of the exercise. This relative number is further converted into an effective exercise time addition $\Delta d_{eff}$ by means of a first conversion function f1. For running, the conversion function can be e.g. of the following form:

$$\Delta d_{eff} = f1(HR, HR_{recovery}, HR_{maxperf}) =$$
$$(\exp(2 * (HR - HR_{recovery})/(HR_{maxperf} - HR_{recovery})) - 1) * coeff$$

In the previous formula $$coeff =$$
$$coeff(HR, HR_{rest}, HR_{max}) = 0.00057 * hrr * hrr - 0.11360 * hrr + 7.34503$$

The exact form of the function also depends on the sports. In the above it has been supposed that the measured pulse HR is higher than the calculated recovery pulse. The constant coefficients shown in the formula are examples.

The function f1 above has been formed using the basic principle that the constant pulse HR is used for reaching the level of maximum performance pulse $HR_{maxperf} = HR$ in a time that corresponds to the world record achieved with the said relative intensity.

The new effective exercise time is the sum of effective exercise time and the addition to the effective exercise time. Thus $$d_{eff\_new} = d_{eff\_old} + \Delta d_{eff}.$$

Thus the weight coefficient function f1 can be a monotonically increasing exponent function in form, determining the accumulation of the effective training time. With such a function it is possible to take the increase of the load of the performance into account especially with higher pulse levels as a larger increase of recovery time, which corresponds well with the reality.

According to one embodiment, any time the pulse exceeds the maximum performance pulse, the recovery time is increased much, i.e. faster than with the pulse being between the recovery pulse and the maximum performance pulse. Such behavior can be modeled, instead of the exponent function of formula f1, with e.g. a linear piecewise function.

The recovery time can be further produced by converting the effective exercise time to recovery time requirement by means of a second conversion function f2. The function f2 can be formed by estimating the recovery requirement from performances of various duration. For example, in running this can be done by tabulating the recovery requirements from maximal performances as a function of distance corresponding to the performance. The recovery requirement calculation may be based on empirical observations about recovery from sports performances. Many factors have an effect on recovery, but fitness level has a considerable effect thereon. Thus the function f2 may be given as $$t_{recovery} = f2(d_{eff}, \text{fitness index, sports}).$$

The triggering event may be based on calculated energy consumption. The energy consumption may be calculated by using the quantity "percentage of pulse reserve", used also in estimating the recovery pulse, as the basic quantity. However, in the energy calculation formula the recovery pulse $HR_{recovery}$ is used instead of the real resting pulse. This gives the effective pulse level $hrr_{eff}$:

$$hrr_{eff} = (HR - HR_{recovery}) * 100\% / (HR_{max} - HR_{recovery}).$$

Using the relative oxygen consumption value the oxygen consumption as percentage of the maximal oxygen intake reserve VO2Max–3.5 ml/kg/min (=% $VO2_{reserve}$) can be calculated and this can be converted to energy consumption, if the index describing the fitness of the person, sex, age and weight are known.

VO2Max can be estimated in a way known to one skilled in the art. For example, VO2Max may be given as $$VO2Max = f(\text{sex, age, fitness index}).$$

When the maximum oxygen intake scale is known, the momentary oxygen consumption value VO2 is produced in units of ml/kg/min.

$$VO2 = (VO2Max - 3.5 \text{ ml/kg/min}) * \% VO2_{reserve} + 3.5 \text{ ml/kg/min}.$$

The value of 3.5 ml/kg/min in the formula corresponds to oxygen consumption in resting state (calculated average) for which also the unit 1 metabolic equivalent of task (MET) is used.

For energy consumption per minute (unit kcal/min) the following formula may be used $$\text{Power} = VO2 * \text{weight} / 200,$$

where weight is the mass of the person in kilograms and VO2 the oxygen consumption in units ml/kg/min.

Triggering event may be based on training effect (TE). Base TE may be calculated as a weighed sum of the level of usage of heartbeat reserve:

$$baseTE = base\ TE(\Sigma w_i * HRReff_i),$$

where i references to a series which is determined based on the heartbeat measurements at predetermined intervals, for example every ten seconds. The $w_i$ is a weighing factor for each $HRReff_i$. An exemplary weighing function has a normal distribution with an average of 33% of HRReff and standard distribution 5% of HRReff. The weighing function can be fixed, i.e. the same for all users, or alternatively adaptable or individually definable to correspond the personal properties of the person.

The calculation of totalTE can be implemented as a combination of the calculations of peakTE and baseTE:

$$totalTE = totalTE(maxstress, \Sigma ww_i * HRRef_i),$$

where $ww_i$ is again a weighing factor for each $HRReff_i$. However, it needs not be the same as in the direct baseTE calculation, i.e. it may be that $w_i \neq ww_i$. The maxstress may be estimated based on HR.

$$maxstress = maxstress(HRReff \text{maxstress}), \text{ and}$$

$$peakTE = peakTE(maxstress).$$

HRReff refers to the person's effective heart rate calculated as the ratio of current heart rate to the difference between the maximum heart rate of the person and a recovery heart rate of the person (the difference thus depicting the available "heart rate reserve" at each moment of time). The recovery heart rate is an estimated heart rate level dynamically updated during the exercise and to which the heart rate of the person recovers in a certain time when the exercise is ended.

Triggering event may be based on excess post-exercise oxygen consumption (EPOC) which may be estimated indirectly based on HR derived information. For example, the EPOC may be estimated at least partly based on training effect TE. Training effect may be defined as described above, or otherwise estimated based on optical blood lactate measurements, for example.

For example, the method comprises receiving, by a wearable device, one or more recipes being indicative of input elements for a computer program code stored in at least one memory of the wearable device, the input elements for the computer program code comprising at least triggering events; display templates corresponding to the triggering events; and content elements corresponding to the triggering events. The method comprises receiving user input for selection of a recipe of the one or more recipes; detecting a first triggering event corresponding to one of the triggering events; and in response to detecting the first triggering event, providing one or more content elements corresponding to the detected first triggering event for display on a display of the wearable device according to a first display template corresponding to the detected first triggering event; detecting a second triggering event corresponding to one of the triggering events; and in response to detecting the second triggering event, providing one or more content elements corresponding to the detected second triggering event for display on a display of the wearable device according to a second display template corresponding to the detected second triggering event. The first display template and the second display template are different.

The invention claimed is:

1. A wearable device, comprising:
    at least one processing core; and
    at least one memory including computer program code;
    the at least one memory and the computer program code configured to, with the at least one processing core, cause the wearable device to:
        receive one or more recipes each being indicative of input elements for the computer program code, the input elements of each recipe comprising at least the following elements :
            i) one or more triggering events;
            ii) one or more display templates corresponding to the one or more triggering events; and
            iii) one or more content elements corresponding to the one or more triggering events;
    and the wearable device is further caused to:
        receive user input for selection of a recipe of the one or more recipes;
        detect a triggering event corresponding to one of the one or more triggering events; and
        in response to detecting the triggering event, provide the one or more content elements corresponding to the detected triggering event for display on a display of the wearable device according to a display template corresponding to the detected triggering event, wherein the display template determines how the content elements are displayed on the display.

2. The wearable device of claim 1, wherein the one or more triggering events are based on one or more of, or based on a quantity derived from one or more of:
- clock time;
- measured time;
- measured distance;
- location;
- altitude;
- heart rate;
- speed;
- pace;
- detected motion;
- temperature;
- input from an external device; and
- user input.

3. The wearable device of claim 1, wherein the one or more triggering events are based on an input from an external device, and wherein the wearable device is configured to be in communication connection with the external device, and the wearable device is further caused to:
- receive an input from the external device via the communication connection; and
- detect the triggering event corresponding to the one or more triggering events based on the received input from the external device or based on a quantity derived using at least the input from the external device.

4. The wearable device of claim 1, wherein the wearable device is caused to:
- start measurement of a workout session; and
- detection of the triggering event is performed during the workout session.

5. The wearable device of claim 1, wherein the one or more recipes are received from a cloud application programming interface and stored into the at least one memory of the wearable device.

6. The wearable device of claim 1, wherein the input elements for the computer program code further comprise one or more actions to be performed by the wearable device in response to detecting the triggering event.

7. The wearable device of claim 1, wherein the input elements for the computer program code further comprise one or more actions to be performed by the wearable device in response to detecting the triggering event, and wherein the action comprises virtually pushing a lap button in response to detecting the triggering event.

8. The wearable device of claim 1, wherein the input elements for the computer program code further comprise one or more actions to be performed by the wearable device in response to detecting the triggering event, and wherein the action comprises activating an alarm in response to detecting the triggering event.

9. The wearable device of claim 1, wherein the input elements for the computer program code further comprise one or more actions to be performed by the wearable device in response to detecting the triggering event, and wherein the action comprises storing data of a current state of the wearable device into the at least one memory of the wearable device.

10. A method comprising:
- receiving, by a wearable device, one or more recipes each being indicative of input elements for a computer program code stored in at least one memory of the wearable device, the input elements of each recipe comprising at least the following elements:
  i) one or more triggering events;
  ii) one or more display templates corresponding to the one or more triggering events; and
  iii) one or more content elements corresponding to the one or more triggering events;

and the method further comprises:
- receiving user input for selection of a recipe of the one or more recipes;
- detecting a triggering event corresponding to one of the one or more triggering events; and
- in response to detecting the triggering event, providing the one or more content elements corresponding to the detected triggering event for display on a display of the wearable device according to a display template corresponding to the detected triggering event, wherein the display template determines how the content elements are displayed on the display.

11. The method of claim 10, wherein the one or more triggering events are based on one or more of, or based on a quantity derived from one or more of:
- clock time;
- measured time;
- measured distance;
- location;
- altitude;
- heart rate;
- speed;
- pace;
- detected motion;
- temperature;
- input from an external device; and
- user input.

12. The method of claim 10, wherein the one or more triggering events are based on an input from an external device, and the method further comprises:
- receiving an input from the external device via a communication connection between the external device and the wearable device; and
- detecting the triggering event corresponding to the one or more triggering events based on the received input from the external device or based on a quantity derived using at least the input from the external device.

13. The method of claim 10, further comprising:
- starting measurement of a workout session; and
- detection of the triggering event is performed during the workout session.

14. The method of claim 10, further comprising:
- receiving the one or more recipes from a cloud application programming interface; and
- storing the one or more recipes into the at least one memory of the wearable device.

15. The method of claim 10, wherein the input elements for the computer program code further comprise at least one action to be performed by the wearable device in response to detecting the triggering event.

16. The method of claim 10, wherein the input elements for the computer program code further comprise at least one action to be performed by the wearable device in response to detecting the triggering event, and wherein the at least one action comprises virtually pushing a lap button in response to detecting the triggering event.

17. The method of claim 10, wherein the input elements for the computer program code further comprise at least one action to be performed by the wearable device in response to detecting the triggering event, and wherein the at least one action comprises activating an alarm in response to detecting the triggering event.

18. The method of claim 10 wherein the input elements for the computer program code further comprise at least one action to be performed by the wearable device in response to detecting the triggering event, and wherein the at least one action comprises storing data of a current state of the wearable device into the at least one memory of the wearable device.

19. The wearable device of claim 1, wherein the recipe does not include executable instructions written in a programming or scripting language.

20. A non-transitory computer readable medium comprising program instructions that, when executed by at least one processor, cause a wearable device to perform a method, the method comprising:

receiving, by a wearable device, one or more recipes each being indicative of input elements for a computer program code stored in at least one memory of the wearable device, the input elements of each recipe comprising at least the following elements:

i) one or more triggering events;

ii) one or more display templates corresponding to the one or more triggering events; and iii) one or more content elements corresponding to the one or more triggering events;

receiving user input for selection of a recipe of the one or more recipes;

detecting a triggering event corresponding to one of the one or more triggering events; and in response to detecting the triggering event, providing the one or more content elements corresponding to the detected triggering event for display on a display of the wearable device according to a display template corresponding to the detected triggering event, wherein the display template determines how the content elements are displayed on the display.

21. The method of claim 10, wherein the recipe does not include executable instructions written in a programming or scripting language.

* * * * *